United States Patent [19]

Fujimoto et al.

[11] Patent Number: 4,481,824
[45] Date of Patent: Nov. 13, 1984

[54] WELD DETECTOR

[75] Inventors: Minoru Fujimoto; Akihiro Tanaka, both of Hitachi, Japan

[73] Assignee: Hitachi, Ltd., Tokyo, Japan

[21] Appl. No.: 411,880

[22] Filed: Aug. 26, 1982

[30] Foreign Application Priority Data

Sep. 4, 1981 [JP] Japan ................. 56-138464

[51] Int. Cl.$^3$ ............................................ G01N 29/00
[52] U.S. Cl. ...................................... 73/643; 73/599; 73/622
[58] Field of Search ................. 73/643, 622, 599, 600

[56] References Cited

U.S. PATENT DOCUMENTS

| 3,321,959 | 5/1967 | Wood et al. | 73/622 |
| 4,289,030 | 9/1981 | Alers et al. | 73/643 |
| 4,348,903 | 9/1982 | Sato et al. | 73/643 |

Primary Examiner—Howard A. Birmiel
Attorney, Agent, or Firm—Antonelli, Terry & Wands

[57] ABSTRACT

A welded steel pipe being turned is subjected to a static magnetic field formed by a sensor. The sensor includes an electromagnet and a transmission and reception coil attached to the end surface of the electromagnet pole facing the steel pipe. The electromagnet is energized by a dc power supply and the transmission coil is supplied a pulse current at certain intervals. As the transmission coil is energized by the pulse current, transverse ultrasonic waves are generated in the steel pipe. The transverse ultrasonic wave propagates through the pipe in the thickness direction thereof and is reflected by the inner surface of the pipe and reaches the outer surface where it is detected by the reception coil. The signal received by the reception coil is amplified by an amplifier and fed to a signal processor which then locates the position of the weld according to the amplitude of the received signals.

20 Claims, 22 Drawing Figures

WELD DETECTOR

BACKGROUND OF THE INVENTION

1. Field of the Invention

The present invention relates to a weld detector to detect a weld of metal material by using electromagnetic ultrasonic waves.

2. Description of the Prior Art

In recent years, with the advancement of welding technique the reliability of the seam of welded steel pipes has greately improved. Since the welded steel pipes are inexpensive compared to the seamless steel pipes, they have come to be widely used as oil well pipes or line pipes. In the fabricating process of the welded steel pipes an inspection is made on the weld of the pipe. The test on the weld includes a water pressure test and an ultrasonic test and in the ultrasonic test the weld must be set at a specified position. The positioning of the weld is done by placing the steel pipe on two turning rollers to rotate the pipe at low speed. To make the weld come to a specified position it is necessary to detect the weld.

Conventionally the detection of the weld has been performed by visual inspection. It is, however, not an easy task even with an experienced inspector to find the weld by checking the steel pipe surface usually and therefore the work efficiency is inevitably low. Thus the automatic detection of the weld has strongly been desired.

In addition to the seamed pipes, the detection of the weld is necessary in adjusting the speed of rollers of the continuous rolling mill in which the steel sheets are welded and rolled continuously.

A known method of automatically detecting the weld is to propagate ultrasonic waves in the metal material and measure the attenuation of the reflected ultrasonic wave to locate the welded portion. This method is described in the specification of Japanese Patent Application (Laid-open No. 50-36186 (1975)), titled "Method and Device for Detecting a Weld of Steel Material". This specification presents a method of distinguishing the weld from the mother plate by putting a piezo-electric type ultrasonic detector in contact with the metal material being checked with a contact medium (water) therebetween, propagating ultrasonic waves into the metal material and measuring the attenuation of the reflected ultrasonic wave.

However, the result of our experiment using the above method showed that almost no difference was observed in the attenuation between the welded and the non-welded portion and therefore the welded portion could not be located.

SUMMARY OF THE INVENTION

The object of this invention is to provide a weld detector which can locate the weld in metal materials without making a contact between the weld and the weld detector, i.e., a non-contact weld detector.

The invention is characterized in that a transverse ultrasonic wave (electromagnetic ultrasonic wave) is generated in the metal material being checked and the signal level of the transverse ultrasonic wave that has traveled through the material is measured to locate the weld.

Other objects and features of this invention will become apparent from the following descriptions.

DESCRIPTION OF THE PREFERRED EMBODIMENT

One example embodiment of this invention will now be described in detail referring to the attached drawings.

Figure 1:
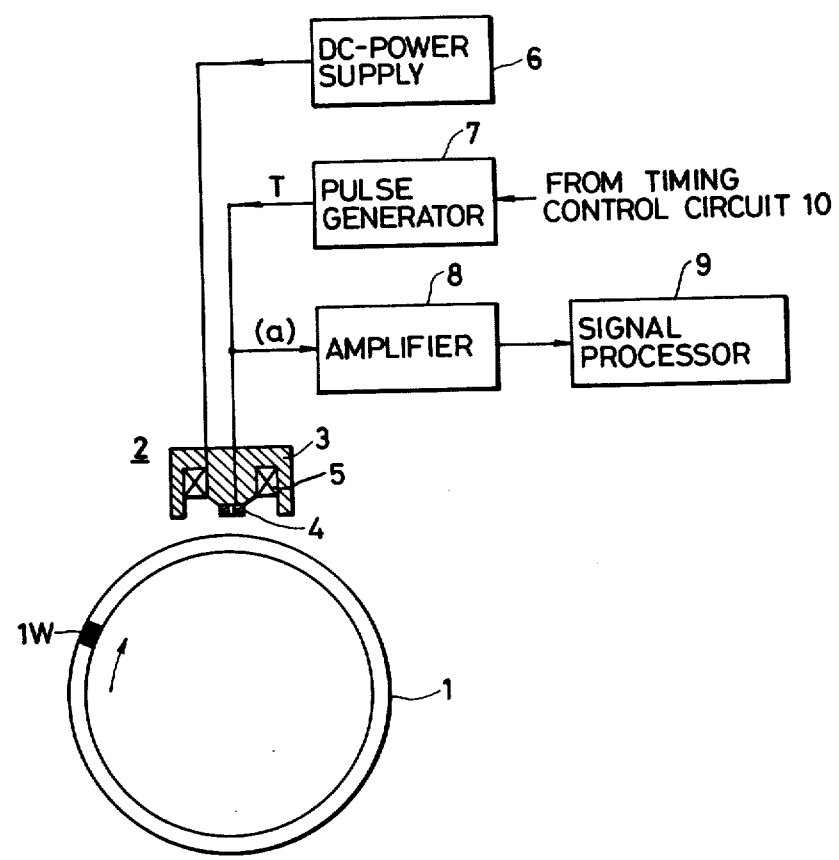
FIG. 1 is a schematic representation of one embodiment of this invention.

FIG. 1 schematically shows the construction of this invention. In this figure a steel pipe 1 is rotated at very low speed by the turning rollers not shown. Placed above the steel pipe 1 is an electromagnetic core 3 which is E-shaped in cross section and has a direct current coil 5 therein. The core 3 has a transmission/reception coil 4 at the end of the central leg facing the steel pipe. The core 3, transmission/reception coil 4 and dc coil 5 make up a sensor 2 which, as described later, can be moved up or down with respect to the steel pipe. The dc coil 5 is energized by the dc power supply 6 and the transmission/reception coil is supplied with a pulse current from pulse generator 7. A signal received by the transmission/reception coil 4 is amplified by the amplifier 8 and fed to the signal processor 9. The amplifier 8 has a limiter circuit at the input to limit the pulse current from the pulse generator 7.

Figure 2:
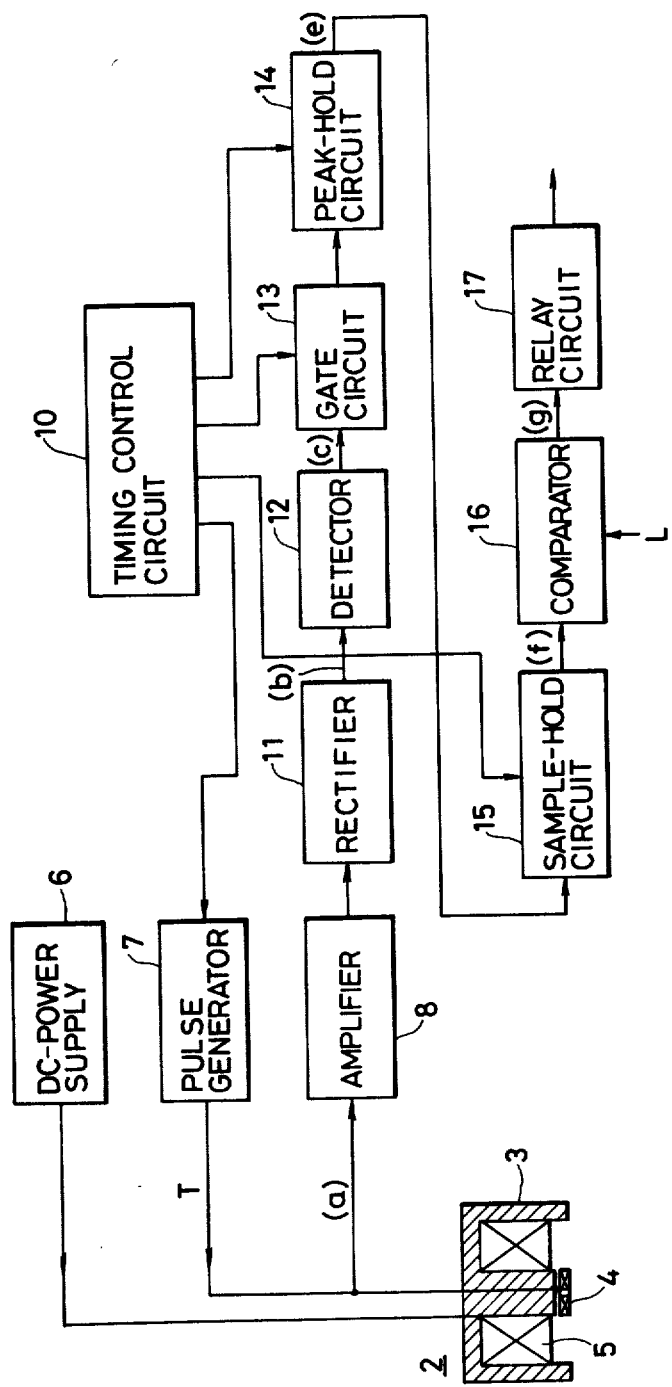
FIG. 2 is a block diagram showing in detail the signal processor as illustrated in FIG. 1.

FIG. 2 shows the detail of the signal processor 9. In this figure, the signal fed from the transmission/reception coil 4 and amplified by the amplifier 8 is rectified by a rectifier 11 and sent to a detector 12. The output of the detector 12 is sent via a gate circuit 13 to a peak-hold circuit 14 where the peak value of the signal is held. The peak value held in the peak-hold circuit is fed to a sample-hold circuit 15 and then to a comparator 16. A timing control circuit 10 controls the timing at which the pulse generator 7 produces pulses, and also determines the on-off timing of the gate circuit 13, the resetting timing of the peak-hold circuit and the sample timing of the sample-hold circuit 15. The comparator 16 produces an output to drive a relay circuit 17 when the received signal level held in the sample-hold circuit 15 is less than a set value L.

Figure 3A:
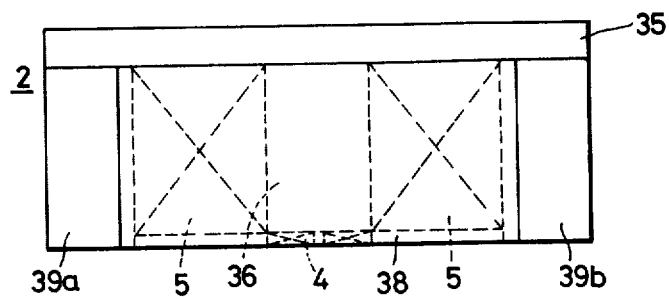
FIGS. 3(a)–(c) represent the construction of the sensor used with the invention, (a) being a plan view, (b) a bottom view and (c) a perspective view.
Figure 3B:
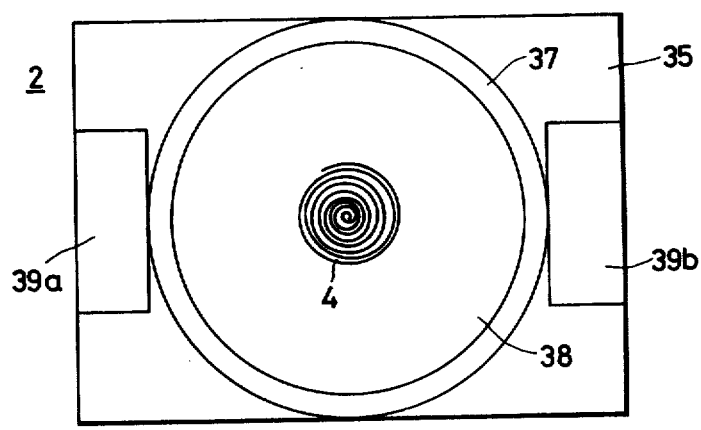
Figure 3C:
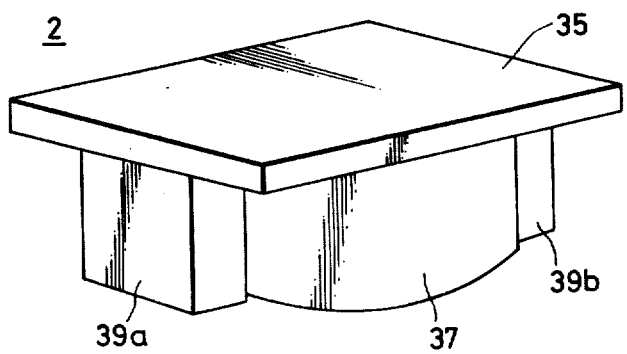

FIG. 3 shows one example construction of the sensor 2. A center leg in the form of circular column (inner magnetic pole) 36 is fixed to the center of the undersurface of a rectangular magnetic plate (iron plate) 35. A protective cylinder 37 is rigidly provided around the center leg 36 and the dc coil 5 is wound in the space between the protective cylinder 37 and the center leg 36. The protective cylinder 37 is formed of magnetic material and serves as an outer magnetic pole and at the same time protects the dc coil 5. The inner magnetic pole 36 is attached with a transmisson/reception coil 4 at the front end. The dc coil 5 is covered with a nonmagnetic disk 38 having a round opening at the center. The disk 38 is fitted into the protective cylinder 37 with the transmission/reception coil 4 positioned at the center opening of the disk 38. Secured to the undersurface of the magnetic plate 35 is a pair of rectangular plates 39a, 39b, which are outer magnetic poles.

Figure 4:
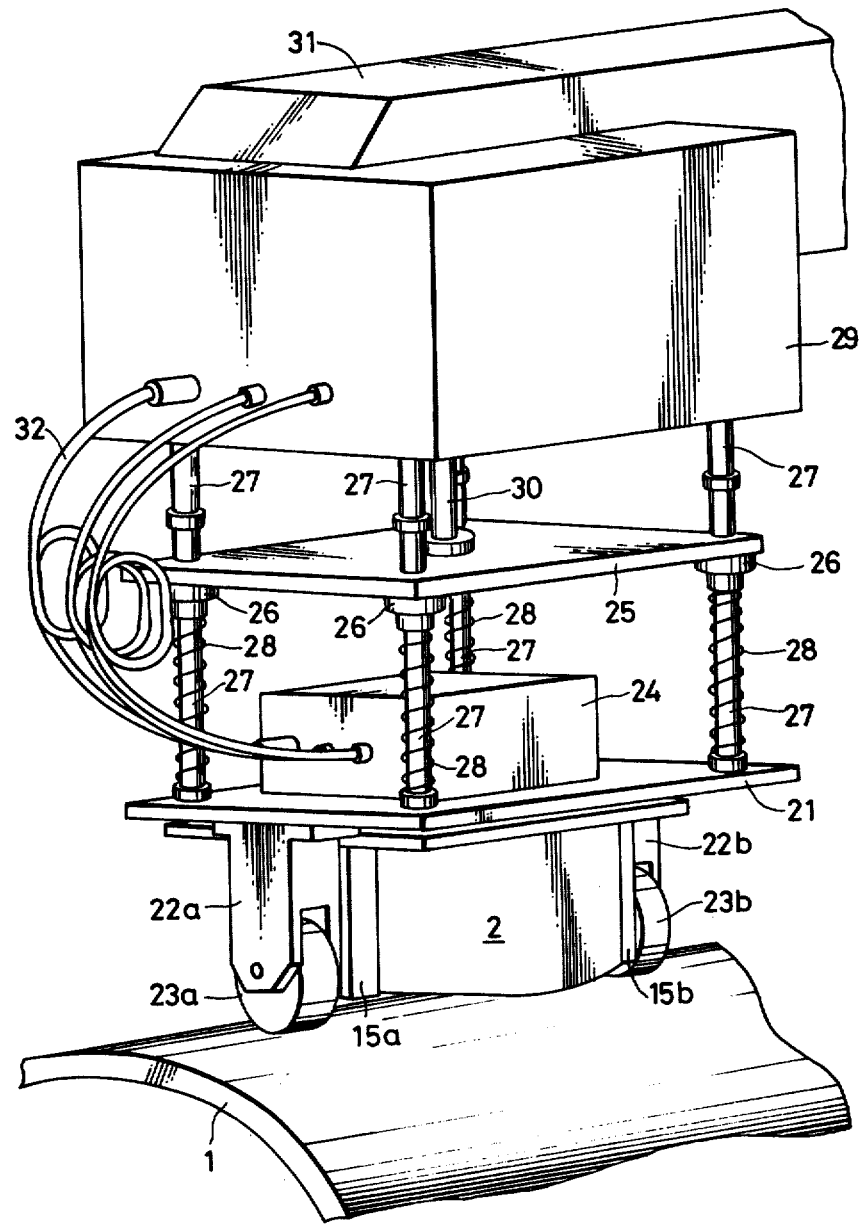
FIG. 4 is a perspective view of a sensor driving mechanism.

FIG. 4 illustrates the mechanism for driving the sensor vertically. As shown in this figure, the sensor 2 is secured by bolt (not shown) to the mounting plate 21 with a certain gap therebetween. The reason that the gap is provided therebetween is to help dissipate heat from the sensor 2. The mounting plate 21 is formed of nonmagnetic material. A pair of roller supporting members 22a, 22b and secured to the undersurface of the mounting plate 21 on each side of the sensor 2 with rollers 23a, 23b supported at the front end of the supporting members 22a, 22b. The rollers 23a, 23b are provided to keep constant the gap between the sensor 2 and the steel pipe 1 as the rollers 23a, 23b move along the surface of the steel pipe 1. A box 24 containing the amplifier 8 is mounted on the upper side of the mounting plate 21. The reason that the amplifier 8 is installed in the box 24 provided near the sensor 2 is that the signal from the transmission/reception coil 4 of the sensor 2 is weak and it must be amplified before being sent to the signal processor 9 of FIG. 1 to mitigate the effect of noise and wire resistance. A drive plate 25 has a similar shape to the mounting plate 21 and has guide washers 26 secured at four corners at the underside thereof to guide sliding rods 27. These four sliding rods 27 are fixed at their lower ends to the four corners of the mounting plate 21. A spring 28 is fitted over each of the four sliding rods 27 between the mounting plate 21 and the drive plate 25.

Rigidly connected to the center of the upper side of the drive plate 25 is one end of a rod 30 of an air cylinder (not shown) installed inside a hollow case 29. The upper portion of each sliding rod 27 is guided to be vertically movable in the hollow case 29. Thus, as the cylinder rod 30 is pushed down, the drive plate 25 compresses the springs 28 bringing the rollers 23a, 23b into tight contact with the surface of the steel pipe 1. The hollow case 29 is mounted to the free end of a suspension arm 31 which is driven upward or downward by a driving means not shown. Reference numeral 32 is a four-wire cable, with two wires used for energizing the dc coil 5 and the other two used for supplying electricity to the amplifier 8. Reference numerals 33 and 34 are coaxial cables, one of which is used to connect the pulse generator 7 and the transmission/reception coil 4 and the other is used to send the output from the amplifier 8 to the signal processor 9 of FIG. 1.

Figure 5:
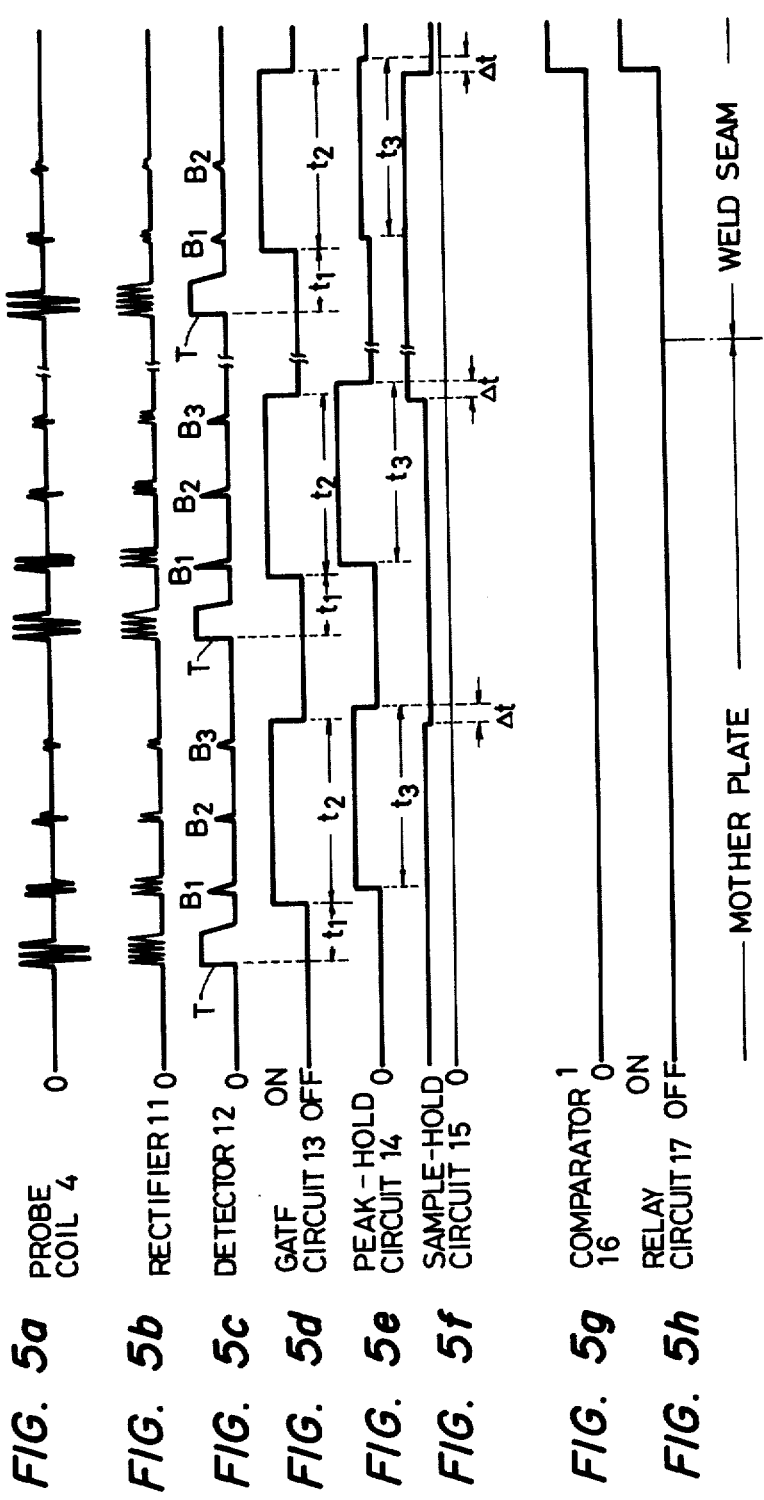
FIGS. 5(a)–(h) and 6(f)–(i) are time charts explaining the operation of this invention.
Figure 6:
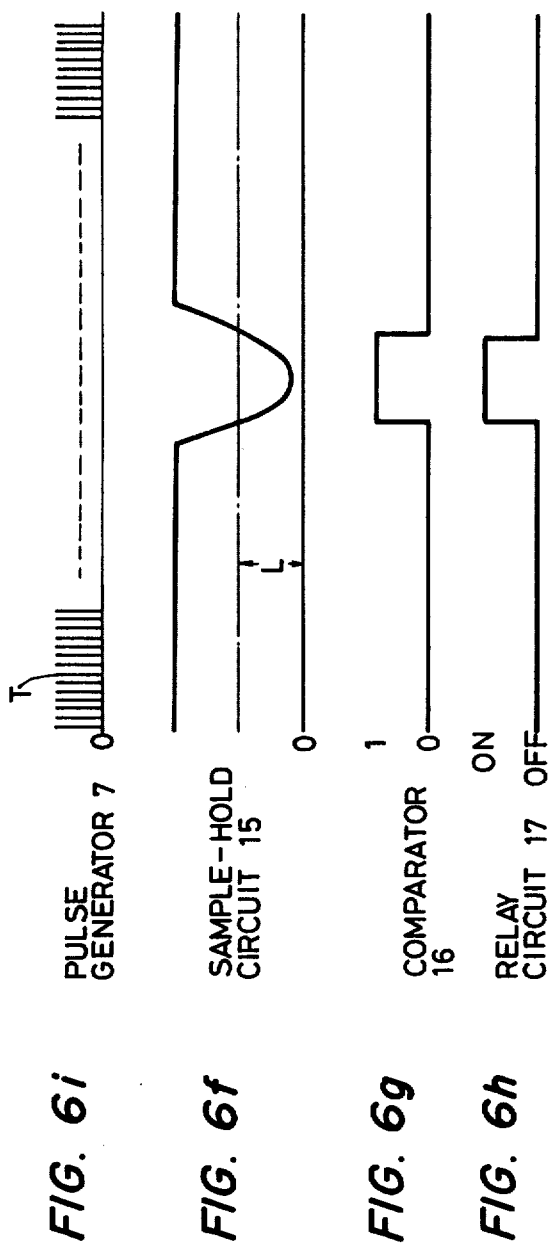

Next, the operation of the signal processor 9 is explained referring to the time charts shown in FIGS. 5 and 6.

With the sensor assuming the position as shown in FIG. 4, the dc coil 5 is energized by the dc power supply 6 to apply the dc magnetic field to the steel pipe 1. In this condition a pulse current from the pulse generator circuit 7 is given to the transmission/reception probe coil 4 to produce by a changing field an eddy current at the surface of the coil 4 facing the steel pipe 1. The combined action of the eddy current and the dc magnetic field produces changing strains at the external surface of the steel pipe 1, which propagates as an ultrasonic wave (of transverse mode) through the pipe thickness. Whether the ultrasonic wave produced is of transverse mode or longitudinal mode depends on the direction of the dc magnetic field crossing the eddy current. To state it more concretely, the ultrasonic wave of transverse mode is generated by the vertical component of the magnetic flux and the ultrasonic wave of longitudinal mode is generated by the horizontal component of the magnetic flux. The position of the transmission/reception coil 4 relative to the electromagnetic poles determines the ratio of transverse and longitudinal components of the ultrasonic wave. When the transmission/reception coil 4 is mounted to the inner magnetic pole as shown in FIG. 3, a large percentage of the ultrasonic wave will consist of the transverse component.

The ultrasonic wave that has propagated through the pipe 1 in the thickness direction from the outer surface is reflected by the inner surface of the pipe 1. When the reflected wave reaches the outer surface of the pipe, the reflected wave (changing strain) will act upon the dc field to induce a current. A change in the field caused by the induced current is detected by the transmisson/reception coil 4, in which a pulse voltage proportional to the change in the field is generated. The ultrasonic wave is attenuated while moving back and forth between the inner and outer surface of the pipe 1.

Pulsating voltages as shown in FIG. 5(a) are induced in the coil 4 each time the sending pulse T from the pulse generator 7 and the reflected waves $B_1$, $B_2$ and $B_3$ reach the outer surface of the pipe 1. The signal received by the transmission/reception coil 4 is amplified by the amplifier 8 and rectified by the rectifier 11. The output of the rectifier is shown in FIG. 5(b). The detector 12 detects the output (b) of the rectifier 11 and produces the output shown in FIG. 5(c). The gate circuit 13, as shown in FIG. 5(d), turns on its gate for a predetermined time interval, a $t_1$ period after the sending pulse T is produced by the pulse generator, to supply the detector output (c) to the peak-hold circuit 14. The timing at which the gate is turned on or off is controlled by the timing control circuit 10. The time $t_1$ is determined considering the duration of the sending pulse T and the time it takes for the first reflected wave to travel through the thickness of the pipe 1 and reach the outer surface of the pipe. The time $t_2$ during which the gate is turned on is determined so that three or four reflected waves will be given to the peak-hold circuit 14. FIG. 5 shows the case where the time $t_2$ is so set as to pass three reflected waves $B_1$, $B_2$ and $B_3$. The reason for supplying a plurality of reflections to the peak-hold circuit 14 is that the level of the second reflection $B_2$ may exceed the first reflection $B_1$ when there is disturbance in waveform. The peak-hold circuit will hold the greatest signal level among the reflected waves $B_1$, $B_2$ and $B_3$. This is shown at FIG. 5(e). The peak-hold circuit 14 retains the peak value for a specified time $t_3$, which is determined by the timing control circuit 10. After having been held for the specified time, the peak value is reset. The sample hold circuit 15 samples the peak value held in the peak-hold circuit which is present $\Delta t$ time prior to the resetting of the peak-hold circuit 14 and retains that value. The output of the sample-hold circuit 15 is shown at FIG. 5(f). The comparator 16 compares the output (f) of the sample-hold circuit 15 and the set value L and generates an output (g) to drive the relay circuit when the output value is smaller than the setting L.

As shown in FIG. 5, the level of the reflected wave for the mother plate is greater than the set value L and no output (g) is produced by the comparator 16. As the pipe 1 turns and the welded portion 1W comes just under the sensor 2, the level of reflection decreases sharply, making the level of the output (f) of the sample-hold circuit 15 smaller than the set value L. This causes the comparator 16 to produce an output (g) driving the relay circuit 17. The operation of the relay circuit represents the detection of the weld.

The above operation is repeated each time the pulse generator 7 produces the sending pulse T. The interval between the sending pulses T is approximately 1 millisecond. The waveforms at the output of the sample hold circuit 15 and the comparator 16 as well as the relay circuit 17 are shown magnified in FIG. 6.

In this way the welded portion is located. Now, we will explain in detail why the level of ultrasonic wave reflected by the weld is substantially reduced.

Figure 7:
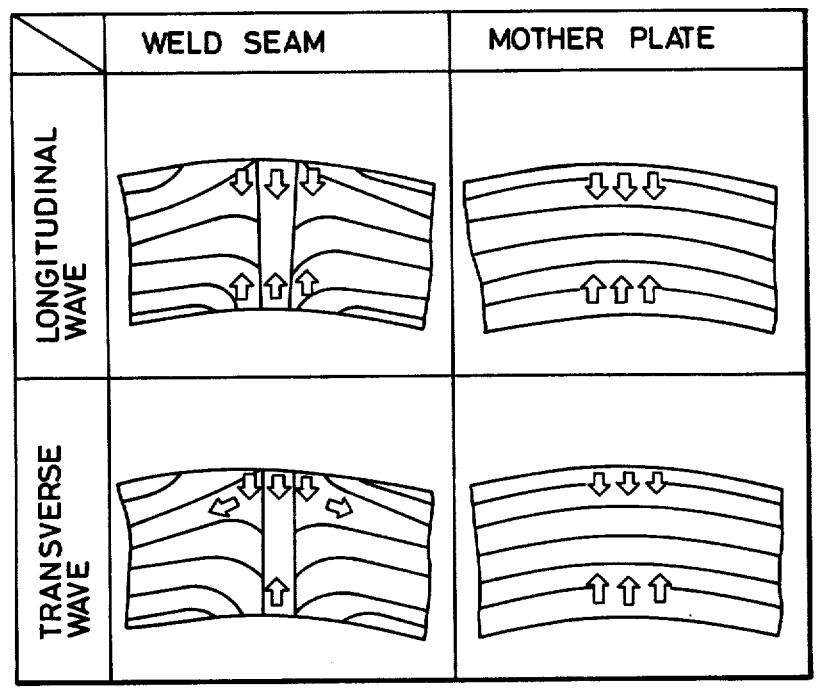
FIGS. 7 and 8 are waveform diagrams explaining the principle of this invention.
Figure 8:
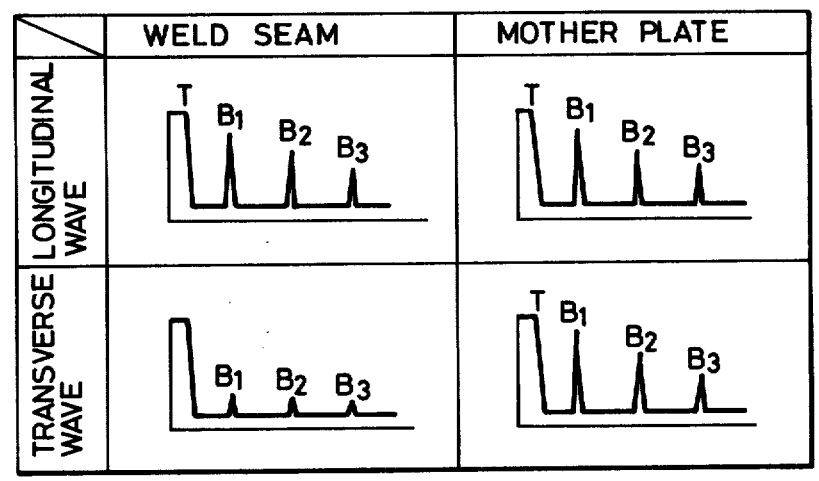

Generally the seamed pipe is manufactured in the following process. A strip of coiled steel is uncoiled and worked by the forming mill and then welded by resistance welding. The structure of the weld seam of the butt-welded steel pipe is shown in FIG. 7. At the weld, the structural layers are raised with the fused portion at the center. On the contrary the other portion not welded (mother plate) has smooth structural layers running parallel to the inner and outer surfaces of the steel pipe.

Figure 9A:
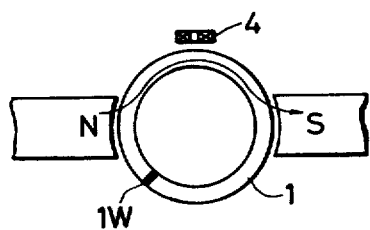
FIGS. 9(a) and (b) are waveform diagrams showing the principle of generating the longitudinal and transverse ultrasonic waves.
Figure 9B:
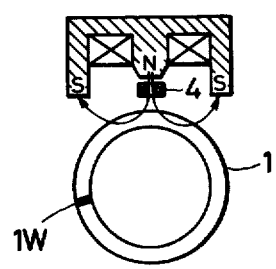

The inventors of this invention conducted an experiment in which the steel pipe was placed in the presence of a magnetic field as shown in FIGS. 9(a) and (b) and the electromagnetic ultrasonic eave of a longitudinal wave (a) and of a transverse wave (b) were applied to the pipe. This experiment showed a conspicuous reduction in the level of reflected transverse ultrasonic waves $B_1$, $B_2$ and $B_3$ at the weld seam. On the other hand, there was no level difference observed in the reflected longitudinal waves $B_1$, $B_2$ and $B_3$ between the weld seam and the non-welded portion. This may be explained as follows. The deformed structural layers serve as a path for the transverse wave and scatters it, while the longitudinal wave is not affected by the structural layers.

The structural layers do not change when the steel pipe is subjected to annealing. Therefore the weld seam can also be located for an annealed steel pipe.

The ultrasonic method of Japanese Laid-Open No. 50-36186 taken as an example of conventional technique uses water as contact medium. From the fact that there can be no transverse wave in liquid it is apparent that the wave used in the above conventional method was a longitudinal wave. This means that no level difference in the reflected waves can result, leaving it impossible to locate the weld seam.

The present invention focuses the attention on the deformed structural layers at the weld and the substantial attenuation of the transverse mode ultrasonic wave reflected at the weld. The ultrasonic wave of transverse mode is produced electromagnetically and applied to the steel pipe with no contact between the sensor and the pipe. This assures accurate detection of the weld.

Further, since the structural layer of the steel pipe is not affected by annealing, the weld portion can be located also for annealed pipes.

While in the above embodiment the dc magnetic field is produced and applied to the steel pipe by the electromagnet, permanent magnets may also be used. It is of course possible to apply this invention to the locating of a weld seam of butt-welded steel sheets in addition to the welded steel pipes.

It should also be noted that while in the above embodiment a single coil of the sensor has both the sending and receiving functions, two separate coils may be provided, each dedicated for a sending or receiving function.

We claim:

1. A weld detector for locating a weld in metal materials comprising: an ultrasonic wave generating means for producing transverse ultrasonic waves electromagnetically for propagation in the metal material from an outer surface toward an inner surface of the metal material in a direction of the thickness of the metal material; an ultrasonic wave detecting means for detecting the transverse ultrasonic waves propagated in the metal material and reflected by the inner surface of the metal material; and signal processor means for processing signals of an amplitude of the reflected transverse ultrasonic waves detected by the ultrasonic wave detecting means to locate the weld according to the amplitude of the detected ultrasonic wave signals.

2. A weld detector as defined in claim 1, wherein the ultrasonic wave generating means is disposed with respect to the outer surface of the metal material for propagating the transverse ultrasonic wave in a direction substantially transverse to the outer surface of the metal material.

3. A weld detector as defined in claim 2, wherein the metal material is in the form of a pipe.

4. A weld detector as defined in claim 2, wherein the metal material is the form of a sheet.

5. A weld detector as defined in claim 2, wherein the ultrasonic wave generating means includes magnet means for applying a static field to the metal material and a transmission coil means attached to an end surface of a pole of the magnet means facing close to the outer surface of the metal material, pulse generator means for supplying pulse current to the transmission coil means for energizing the transmission coil means for producing the transverse ultrasonic waves for propagation in the metal material, the ultrasonic wave detecting means including reception coil means attached to the end surface of the pole of the magnet means for detecting the transverse ultrasonic waves reflected by the inner surface of the metal material and providing an output signal indicative thereof.

6. A weld detector as defined in claim 5, wherein the magnet means is an electromagnet within a dc coil.

7. A weld detector as defined in claim 5, wherein the magnet means is a permanent magnet.

8. A weld detector as defined in claim 5, wherein the transmission coil means and the reception coil means is formed as a single coil.

9. A weld detector as defined in claim 5, wherein the signal processing means includes amplifying means for amplifying the reflected transverse ultrasonic wave signals detected by the reception coil means each time the ultrasonic wave is reflected by the inner surface of the metal material and reaches the outer surface of the metal material, memory means for storing the maximum amplitude of the reflected wave signals amplified by the amplifier means for one cycle in which the pulse generator means supplies a pulse current, and comparator means for comparing the amplitude signal level stored in the memory means and a set value for each cycle of pulse current and for providing an output indicative of the weld in accordance therewith.

10. A weld detector as defined in claim 9, wherein the amplifying means is disposed proximate to the reception coil means.

11. A weld detector as defined in claim 9, wherein means are provided for maintaining a constant spacing between the outer surface of the metal material and the end surface of the pole of the magnet means facing the outer surface of the metal material.

12. A weld detector for locating a weld in metal materials comprising: a sensor having a magnet means for applying a static field to the steel pipe and a transmission and reception coil attached to an end surface of a pole of the magnet means facing close to the steel pipe surface, a pulse generator for supplying pulse current to the transmission coil to energize the transmission coil and produce transverse ultrasonic waves for propagation in the metal material in a direction of the thickness of the metal material; and a signal process for processing signals of reflected transverse ultrasonic waves propagated in the metal material and detected by the reception coil, the signal processor locating the weld according to the amplitude of the detected ultrasonic wave signals.

13. A weld detector as defined in claim 12, wherein the magnet means is an electromagnet having a dc coil.

14. A weld detector as defined in claim 12, wherein the magnet means is a permanent magnet.

15. A weld detector as defined in claim 12, wherein the transmission and detection reception coil is formed of a single coil.

16. A weld detector for locating a weld in steel pipes comprising: a welded steel pipe which is rotated; a sensor having an electromagnet for applying a static field to the steel pipe and a transmission and reception coil attached to an end surface of an electromagnet pole facing close to the steel pipe surface; a dc power source for energizing a dc coil of the electromagnet; a pulse generator for supplying pulse current to the transmission coil to energize the coil and generate transverse ultrasonic waves for propagation in the steel pipe in a direction of the thickness of the steel pipe; and a signal processor for processing signals of reflected transverse ultrasonic waves propagated in the thickness direction of the steep pipe and detected by the reception coil, the signal processor locating the weld in the steel pipe according to the amplitude of the signals detected by the reception coil.

17. A weld detector as defined in claim 16, wherein the sensor has rollers to keep constant the gap between the steel pipe surface and an end surface of a pole of the electromagnet facing the pipe as the sensor moves over the surface of the steel pipe.

18. A weld detector as defined in claim 16, further comprising means for driving the sensor up or down with respect to the steel pipe.

19. A weld detector for locating a weld in steel pipes comprising: a welded steel pipe which is rotated; a sensor having an electromagnet for applying a static field to the steel pipe and a transmission and reception coil attached to the end surface of the electromagnet pole facing close to the steel pipe surface; a dc power supply for energizing a dc coil of the electromagnet; a pulse generator for supplying pulse current to the transmission coil to energize the coil and produce a transverse ultrasonic wave in the steep pipe for propagation in a direction of the thickness of the steel pipe from an outer surface toward an inner surface of the steel pipe; an amplifier for amplifying the reflected transverse ultrasonic wave signal detected by the reception coil each time the ultrasonic wave is reflected by the inner surface of the steel pipe and reaches the outer surface; a memory means for storing the maximum amplitude of the reflected wave signals amplified by the amplifier for one cycle in which the pulse generator supplies a pulse current; and a comparator means for comparing the amplitude signal level stored in the memory means and a set value for each cycle of the pulse current.

20. A weld detector as defined in claim 19, wherein the amplifier is provided close to the sensor.

* * * * *